United States Patent [19]

Zasloff et al.

[11] Patent Number: 5,254,535
[45] Date of Patent: Oct. 19, 1993

[54] COMPOSITION AND TREATMENT WITH BIOLOGICALLY ACTIVE PEPTIDES AND ANTIBIOTIC

[75] Inventors: Michael Zasloff, Merion Station; Barry Berkowitz, Ft. Washington, both of Pa.

[73] Assignee: The Children's Hospital of Pennsylvania, Philadelphia, Pa.

[21] Appl. No.: 402,642

[22] Filed: Sep. 5, 1989

Related U.S. Application Data

[63] Continuation-in-part of Ser. No. 339,292, Apr. 17, 1989, abandoned.

[51] Int. Cl.[5] ................... A61K 37/02; C07K 7/08; C07K 7/10
[52] U.S. Cl. ................................. 514/12; 514/13; 514/14
[58] Field of Search .......................... 514/12, 13, 14

[56] References Cited

U.S. PATENT DOCUMENTS

| | | | |
|---|---|---|---|
| 4,107,298 | 8/1978 | Luning | 530/326 |
| 4,617,149 | 10/1986 | DiMarchi et al. | 530/324 |
| 4,636,489 | 1/1987 | Sumuller et al. | 530/324 |
| 4,659,692 | 4/1987 | Lehrer et al. | 530/324 |
| 4,668,662 | 5/1987 | Tripier | 530/324 |
| 4,791,100 | 12/1988 | Kramer et al. | 530/324 |

OTHER PUBLICATIONS

B. Christensen, et al., "Channel-forming properties of cecropins and related model compounds incorporated into planar lipid membranes," *Proc. Natl. Acad. Sci.*, vol. 85, pp. 5072–5076, Jul. 1988.

Merrifield, "Solid Phase Peptide Synthesis," *Journal of the American Chemical Society*, vol. 85, pp. 2149–2154 (1963).

Zasloff, "Magainins, a class of antimicrobial peptides from Xenopus skin: Isolation, characterization of two active forms, and partial cDNA sequence of a precursor," *Proc. Natl. Acad. Sci.*, vol. 84 pp. 5449–5453, Aug. 1987.

Hoffman, et al., "A novel peptide designated PYLa and its precursor as predicted from cloned mRNA of Xenopus laevis skin," *The EMBO Journal*, vol. 2 No. 5 pp. 711–714 (1983).

Andreu, et al., *J. Biochem.* 149:531–535, 1985.

Gibson, et al., "Novel Peptide Fragments Originating from PGLa and the Caerulein and Xenopsin Precursors from Xenopus laevis," *J. Biol. Chem.* 261:5341–5349, 1986.

Giovanni, et al., "Biosynthesis and degradation of peptides derived from Xenopus laevis prohormones," *Biochem. J.* 243:113–120, 1987.

Richter, et al., *J. Biol. Chem.* 261, 3676–3680 (1986).

Wakabayashi, et al., "Complete nucleotide sequence of mRNA for caerulein precursor from Xenopus skin: the mRNA contains an unusual repetitive structure," *Nucleic Acids Research*, vol. 13, No. 6, pp. 1817–1828 (1985).

Boman, et al., "Cell-Free Immunity in Insects," *Ann. Rev. Microbiol.* 41:103-26 (1987).

*Molecular Entomology*, pp. 369–378, in particular p. 375, Alan R. Liss Inc. (1987).

Vaara, et al., Antimicrobia Agents and Chemotherapy, vol. 24, No. pp. 107–113 (Jul. 1983).

Viljanen, et al., Antimicrobial Agents and Chemotherapy vol. 25, No. 6, pp. 701–705 (Jun. 1984).

Viljanen, et al., Can. J. Microbiol., vol. 32, pp. 66–69 (1986).

*Primary Examiner*—Lester L. Lee
*Attorney, Agent, or Firm*—Woodcock Washburn Kurtz Mackiewicz & Norris

[57] ABSTRACT

A composition comprising at least one biologically active amphiphilic peptide, said peptide being an ion channel-forming peptide, and an antibiotic selected from the class consiting of bacitracins, aminoglycosides, penicillins, monobactams, hydrophobic antibiotics, 50-S ribosome inhibitors, antibiotics having a large lipid like lactone ring, and derivatives or analogues thereof. The biologically active amphiphilic peptide and the antibiotic may be administered in amounts effective to inhibit growth of a target cell. The biologically active amphiphilic peptide and antibiotic may potentiate each other.

77 Claims, No Drawings

COMPOSITION AND TREATMENT WITH BIOLOGICALLY ACTIVE PEPTIDES AND ANTIBIOTIC

This application is a continuation-in-part of application Ser. No. 339,292, filed Apr. 17, 1989, and now abandoned.

This invention relates to biologically active peptides, and more particularly to compositions and uses involving biologically active peptides and an antibiotic; in particular an antibiotic selected from the class consisting of bacitracins, aminoglycosides, hydrophobic antibiotics, penicillins, monobactams or derivatives or analogues thereof.

It has been disclosed that agents such as polymyxin B nonapeptide, which disrupt the outer membrane of Gram-negative bacteria, increase the potency of certain antibiotics, such as fusidic acid, novobiocin, and erythromycin, against the organisms Viljanen, et al, "Susceptibility of Gram-Negative Bacteria to Polymyxin B Nonapeptide," *Antimicrobial Agents and Chemotherapy*, Vol. 25, No. 6, Pgs. 701-705 (June 1984). Viljanen, et al, in "Susceptbility of Gram-Negative Bacteria to the Synergistic Bactericidal Action of Serum and Polymyxin B Nonapeptide," *Can. J. Microbiol*. Vol. 32 pgs. 66-69 (1986), disclose a synergistic effect of polymyxin B nonapeptide and serum in bactericidal action against *E. coli* strains, strains of *Salmonella typhimurium*, Klebisiella species, *Enterobacter cloacae, Pseudomonas influenzae*. Vaara, et al., have disclosed a synergistic effect of polymyxin B nonapeptide and novobiocin, fusidic acid, erythromycin, clindamycin, nafcillin, and cloxacillin against smooth encapsulated *E. coli* and smooth *Salmonella typhimurium. Antimicrobial Agents and Chemotherapy*, Vol. 24, No. 1, pgs. 107-113. (July 1983).

In accordance with an aspect of the present invention, there is provided a composition which includes at least one biologically active amphiphilic peptide; and an antibiotic; in particular an antibiotic selected from the group comprising bacitracins, aminoglycosides, hydrophobic antibiotics (including but not limited to erythromycin and derivatives or analogues thereof), penicillins, monobactams, or derivatives or analogues thereof.

In accordance with another aspect of the present invention, there is provided a process wherein there is administered to a host at least one biologically active amphiphilic peptide; and an antibiotic; in particular an antibiotic selected from the group comprising bacitracins, aminoglycosides, hydrophobic antibiotics (including but not limited to erythromycin and derivatives or analogues thereof), penicillins, monobactams, or derivatives or analogues thereof.

Although the invention is not to be limited to any theoretical reasoning, it is believed that the peptides employed in the present invention interact with the membranes of bacterial cells and such interaction enhances the ability of the above-mentioned antibiotics to cross the membrane. It is to be understood, however, that the scope of the invention is not limited to such antibiotics.

The bacitracins, and derivatives and analogues thereof, are a group of polypeptide antibiotics. A preferred bacitracin is bacitracin A.

Aminoglycoside antibiotics include tobramycin, kanamycin, amikacin, the gentamicins (e.g., gentamicin $C_1$, gentamicin $C_2$, gentamicin $C_{1a}$), netilmicin, kanamycin, and gramacidin, polymyxin, vancomycin, and teichoplanin and derivatives and analogues thereof. The preferred aminoglycosides are tobramycin and the gentamicins. The aminoglycosides, and the bacitracins hereinabove described, tend to be hydrophilic and water-soluble.

Penicillins which may be employed in accordance with the present invention include, but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides such as erythromycin, roxythromycin, clarithromycin, etc.; 9-N-alkyl derivatives of erythromycin; midecamycin acetate; azithromycin; flurithromycin; rifabutin; rokitamycin; a 6-O-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolide ring known as A-62514 (Abbott); AC-7230 (Toyo Jozo); benzoxazinorifamycin; difficidin; dirithromycin; a 3-N-piperdinomethylzaino methyl rifamycin SV known as FCE-22250 (Farmitalia); M-119-a (Kirin Brewery); a 6-O-methyl-1-4"-O-carbamoyl erythromycin known as A-63075 (Abbott); 3-formylrifamycin SV-hydrazones with diazabicycloalkyl side chains such as CGP-27557 and CGP-2986 (Ciba-Geigy); and 16-membered macrolides having a 3-O-alpha-L-cladinosyl moiety, such as 3-O-alpha-L-cladinosyldeepoxy rosaramicin; tylosins and acyl demycinosyl tylosins.

In addition to the macrolides hereinabove described, rifamycin, carbenicillin, and nafcillin may be employed as well.

Other antibiotics which may be used (whether or not hydrophobic) are antibiotics which are 50-S ribosome inhibitors such as lincomycin; clindamycin; and chloramphenicol; etc.; antibiotics which have a large lipid like lactone ring, such as mystatin; pimaricin, etc.

The preferred hydrophobic antibiotics are the macrolides and in particular erythromycin and derivatives and analogues thereof.

The biologically active amphiphilic peptides employed in the present invention are generally water soluble to a concentration of at least 20 mg/ml at neutral pH in water. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure. Such peptides are also preferably non-hemolytic; i.e.; they will not rupture blood cells at effective concentrations.

In general, such peptides have at least 16 amino acids, and preferably at least 20 amino acids. In most cases, such peptides do not have in excess of 50 amino acids.

In general, the biologically active petpdies employed in the present invention are ion channel-forming peptides. An ion channel-forming peptide or ionophore is a peptide which increases the permeability for ions across a natural or synthetic lipid membrane. B. Christensen et al. PNAS Vol. 85 P. 5072-76 (July, 1988) describes methodology which indicates whether or not a peptide has ion channel-forming properties and is therefore an ionophore. As used herein an ion channel-forming peptide is a peptide which has ion channel-forming properties as determined by the method of Christensen et al. In most cases, the ion channel forming peptides used in the present invention are anion channel forming peptides (the peptides increase the permeability of anions) as determined by the method of Christensen et al.

An amphiphilic peptide is a peptide which includes both hydrophobic and hydrophilic peptide regions.

Although the biologically active amphiphilic (amphipathic) ion channel-forming peptides are capable of forming ion channels, the ability of such peptides and the above-mentioned antibiotics to potentiate each other is not necessarily dependent upon the antibiotic crossing a membrane through such channels. Thus, although the ability to form ion channels may be a characteristic of a type of peptide used in the invention, the invention is not limited to the formation and/or use of such channels as part of the mechanism for the peptide potentiating the antibiotic or vice versa. Similarly, although Applicant believes that such peptides interact with the membrane of bacterial cells and such interaction is the mechanism by which the antibiotic potentiates the peptide and vice versa, the present invention is not limited to such a mechanism.

The term "potentiate", as used herein, means either that the biologically active amphiphilic peptide is effective in increasing the biological activity of the above-mentioned antibiotics against a target cell so thereby the antibiotic may be employed in an amount lower than which would be required for preventing, destroying or inhibiting growth of a target cell, and/or that the peptide may be employed in an amount lower than which would be required for preventing, destroying, or inhibiting growth of a target cell.

The administration of the biologically active amphiphilic peptides and antibiotic to a target cell may be direct administration to the cell or systemic or topical administration to a host which includes the target cell, in order to prevent, destroy, or inhibit the growth of a target cell. Target cells whose growth may be prevented, inhibited, or destroyed by the administration of the biologically active amphiphilic peptide and antibiotic include Gram-positive and Gram-negative bacteria.

For example, erythromycin, when employed without the above-mentioned peptides, is effective only against Gram-positive organisms. Applicants have found unexpectedly that erythromycin, when employed in combination with the above-mentioned peptides, is potentiated such that it becomes biologically effective against Gram-negative bacteria. Moreover, the erythromycin may be employed against Gram-positive bacteria in amounts lower than those normally used. Furthermore, such a result can be achieved by using peptide amounts lower than those normally used.

The peptides employed in the present invention are capable of interacting selectively with membranes of bacteria.

In general, the peptide is employed to provide peptide dosages of from 1 mg to 500 mg per kilogram of host weight, when administered systemically. When administered topically, the peptide is used in a concentration of from 0.1% to 10%.

The antibiotic, such as those hereinabove described, or derivatives or analogues thereof, when used topically, is generally employed in a concentration of about 0.1% to about 10%. When used systemically, the antibiotic or derivative or analogue thereof is generally employed in an amount of from 1.25 mg to about 45 mg per kg of host weight per day.

The use of a combination of peptide and an antibiotic such as those hereinabove described, or derivatives or analogues thereof in accordance with the present invention is effective as an antibiotic, and may be employed to inhibit, prevent or destroy the growth or proliferation of microbes, such as bacteria.

The compositions have a broad range of potent antibiotic activity against a plurality of microorganisms, including Gram-positive and Gram-negative bacteria. Such compositions may be employed for treating or controlling microbial infection caused by organisms which are sensitive to such composition. The treatment may comprise administering to a host organism or tissues acceptable to or affiliated with a microbial infection an anti-microbial amount of such peptide and an antibiotic.

The compositions may also be used as preservatives or sterilants for materials susceptible to microbial contamination.

In accordance with a preferred embodiment, the peptide used in conjunction with an antibiotic such as those hereinabove described, or derivatives or analogues thereof is a basic (positively charged) polypeptide having at least sixteen amino acids wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acid, with such groups of two hydrophilic amino acids being spaced from each other by at least one amino acid other than a hydrophilic amino acid (preferably at least two amino acids) and generally no greater than four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids. Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of Ala, Cys, Phe, Gly, Ile, Leu, Met, Val, Trp, and Tyr. The neutral hydrophilic amino acids may be selected from the class consisting of Asn, Gln, Ser, and Thr. The basic hydrophilic amino acids may be selected from the class consisting of Lys, Arg, and His.

Each of the groups of four amino acids may be of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different. In a preferred embodiment, the polypeptide chain may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary provided that in each group of the at least four groups of amino acids there are two hydrophobic and two hydrophilic amino acids as hereinabove noted.

Thus, in a preferred embodiment, the biologically active polypeptide comprises a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic amino acids, one of C or D is basic hydrophilic amino acid, and the other of C or D is basic or neutral hydrophilic amino acid. The resulting polypeptide chain, therefore, may have one of the following sequences:

$(X_1)_a(A\text{-}B\text{-}C\text{-}D)_n(Y_1)_b$ $(X_2)_a(B\text{-}C\text{-}D\text{-}A)_n(Y_2)_b$ $(X_3)_a(C\text{-}D\text{-}A\text{-}B)_n(Y_3)_b$ $(X_4)_a(D\text{-}A\text{-}B\text{-}C)_n(Y_4)_b$ wherein
 $X_1$ is D; C-D- or B-C-D-, $Y_1$ is -A or -A-B or -A-B-C
 $X_2$ is A-, D-A- or C-D-A-
 $Y_2$ is -B, -B-C or B-C-D
 $X_3$ is B-, A-B-, D-A-B-
 $Y_3$ is -C, -C-D, -C-D-A
 $X_4$ is C-, B-C-, A-B-C-
 $Y_4$ is -D, -D-A, -D-A-B
 a is 0 or 1; b is 0 or 1 and
 n is at least 4.

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and do not adversely affect the folding characteristics of the chain to that which is significantly different from one in which the hereinabove noted group of four amino acids are not spaced from each other.

As representative examples of peptides in accordance with the present invention, there may be mentioned.
 I Ala-Phe-Ser-Lys-Ala-Phe-Ser-Lys-Ala-Phe-Ser-Lys-Ala-Phe-Ser-Lys-Ala-Phe-Ser-Lys
 II Ala-Phe-Ser-Lys-Ala-Phe-Ser-Lys-Ala-Phe-Ser-Lys-Ala-Phe-Ser-Lys-Ala-Phe-Ser-Lys-Ala-Phe-Ser-Lys.
 III Phe-Ser-Lys-Ala-Phe-Ser-Lys-Ala-Phe-Ser-Lys-Ala-Phe-Ser-Lys-Ala-
 IV Ser-Lys-Ala-Phe-Ser-Lys-Ala-Phe-Ser-Lys-Ala-Phe-Ser-Lys-Ala-Phe-Ser-Lys-Ala-Phe-
 V Lys-Ala-Phe-Ser-Lys-Ala-Phe-Ser-Lys-Ala-Phe-Ser-Lys-Ala-Phe-Ser The peptide may have amino acids extending from either end of the chain. For example, the chains may have a Ser-Lys sequence before the "Ala" end, and/or an Ala-Phe sequence after the "Lys" end. Other amino acid sequences may also be attached to the "Ala" and/or the "Lys" end.

Similarly, in any polypeptide chain having at least four groups of amino acids of the sequence as described above, the chain may have, for example, a C-D sequence before the first A-B-C-D group. Also other amino acid sequences may be attached to the "A" and/or the "D" end of one of these polypeptide chains. Also there may be amino acids in the chain which space one or more groups of the hereinabove noted four amino acids from each other.

The peptides may be produced by known techniques and obtained in substantially pure form. For example, the peptides may be synthesized on an automatic synthesizer. *Journal of the American Chemical Society*, Vol. 85 Pages 2149–54(1963). It is also possible to produce such peptides by genetic engineering techniques.

In accordance with another preferred embodiment, the peptide employed in conjunction with an antibiotic such as those hereinabove described, or derivatives or analogues thereof may be a magainin peptide.

A magainin peptide is either a magainin such as Magainin I, II or III or an analogue or derivative thereof. The magainin peptides may include the following basic peptide structure $X_{12}$ $R_{11}\text{-}R_{11}\text{-}R_{12}\text{-}R_{13}\text{-}R_{11}\text{-}R_{14}\text{-}R_{12}\text{-}R_{11}\text{-}R_{14}\text{-}R_{12}\text{-}R_{11}\text{--}$
$R_{11}\text{-}R_{11}\text{-}R_{14a}\text{-}(R_{15})_n\text{-}R_{14a}\text{-}R_{14}\text{--}$ wherein $R_{11}$ is a hydrophobic amino acid, $R_{12}$ is a basic hydrophilic amino acid; $R_{13}$ is a hydrophobic, neutral hydrophilic, or basic hydrophilic amino acid; $R_{14}$ and $R_{14a}$ are hydrophobic or basic hydrophilic amino acids, $R_{15}$ is glutamic acid or aspartic acid, or a hydrophobic or basic hydrophilic amino acid, and n is 0 or 1. In a preferred embodiment, $R_{13}$ is a hydrophobic or neutral hydrophilic amino acid, $R_{14a}$ is a hydrophobic amino acid, and $R_{15}$ is glutamic acid or aspartic acid.

Thus, for example, a magainin peptide may include the following structure:

$Y_{12}\text{-}X_{12}$, where $X_{12}$ is the hereinabove described basic peptide structure and $Y_{12}$ is
 (i) $R_{12}$
 (ii) $R_{14a}\text{-}R_{12}$;
 (iii) $R_{11}\text{-}R_{14a}\text{-}R_{12}$; or
 (iv) $R_{14}\text{-}R_{11}\text{-}R_{14a}\text{-}R_{12}$
where $R_{11}$, $R_{12}$, $R_{14}$, and $R_{14a}$ are as previously defined.

A magainin peptide may also have the following structure:

$\text{-}X_{12}\text{-}Z_{12}\text{-}$ wherein $X_{12}$ is as previously defined and $Z_{12}$ is:
  (i) $R_{16}$ where $R_{16}$ is a basic hydrophilic amino acid or asparagine or glutamine; or
  (ii) $R_{16}$-$R_{17}$ where $R_{17}$ is a neutral hydrophilic amino acid, a hydrophobic amino acid, or a basic hydrophilic amino acid. Preferably, $R_{17}$ is a neutral hydrophilic amino acid.

A magainin peptide may also have the following structure:

$$(Y_{12})_a\text{-}X_{12}\text{-}(Z_{12})_b$$

where $X_{12}$, $Y_{12}$, and $Z_{12}$ are as previously defined, and a is 0 or 1 and b is 0 or 1.

The magainin peptides may also include the following basic peptide structure $X_{13}$:

$$R_{14}\text{-}R_{11}\text{-}R_{14a}\text{-}R_{12}\text{-}R_{11}\text{-}R_{11}\text{-}R_{12}\text{-}R_{13}\text{-}R_{11}\text{-}R_{14}\text{-}R_{12}\text{-}R_{11}\text{-}R_{11}\text{-}R_{12}\text{-},$$

wherein $R_{11}$, $R_{12}$, $R_{13}$, $R_{14}$, and $R_{14a}$ are amino acids as hereinabove described.

The magainin peptide may also include the following structure $X_{13}$-$Z_{13}$; wherein $X_{13}$ is the hereinabove described basic peptide structure and $Z_{13}$ is $$(R_{11})_n\text{-}(R_{11})_n\text{-}(R_{11})_n\text{-}(R_{14a})_n\text{-}(R_{15})_n\text{-}(R_{14a})_n\text{-}(R_{14})_n\text{-}(R_{16})_n\text{-}(R_{17})_n\text{-},$$

wherein $R_{11}$, $R_{14}$, $R_{14a}$, $R_{15}$, $R_{16}$, and $R_{17}$ are amino acids as hereinabove described, and n is 0 or 1, and each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequence (expressed as a single letter code) as well as appropriate analogues and derivatives thereof:
  (a) (NH$_2$) GIGKFLHSAGKFGKAFVGEIMKS (OH) or (NH$_2$) (Magainin I)
  (b) (NH$_2$) GIGKFLHSAKKFGKAFVGEIMNS (OH) or (NH$_2$) (Magainin II)
  (c) (NH$_2$) GIGKFLHSAKKFGKAFVGEIMN (OH) or (NH$_2$) (Magainin III)

The following are examples of peptide derivatives or analogs of the basic structure:
  (d) (NH$_2$) IGKFLHSAKKFGKAFVGEIMNS(OH) or (NH$_2$)
  (e) (NH$_2$) GKFLHSAKKFGKAFVGEIMNS(OH) or (NH$_2$)
  (f) (NH$_2$) KFLHSAKKFGKAFVGEIMNS(OH) or (NH$_2$)

Magainin peptides are described in *Proc. Natl. Acad Sci.* Vol. 84 pp. 5449-53 (August 1987). The term "magainin peptides" as used herein refers to the basic magainin structure as well as derivatives and analogs thereof, including but not limited to the representative derivatives or analogs.

In accordance with a further embodiment, the peptide employed in conjunction with an antibiotic such as bacitracin, tobramycin or gentamicin or derivatives or analogues thereof may be a PGLa peptide or an XPF peptide.

A PGLa peptide is either PGLa or an analogue or derivative thereof. The PGLa peptides preferably include the following basic peptide structure $X_{14}$:

$$\begin{array}{c}-R_{11}-R_{17}-R_{12}-R_{11}-R_{14}-R_{11}-R_{11}-\\R_{11}-R_{14}-R_{12}-R_{11}-R_{11}-R_{12}-R_{11}-\\R_{11}-R_{11}-R_{12}-\end{array}$$

where $R_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl end.

Thus, for example, a PGLa peptide may have the following structure:

$$\text{-}Y_{14}\text{-}X_{14}\text{-}$$

where $X_{14}$ is as previously defined and $Y_{14}$ is
  (i) $R_{11}$;
  (ii) $R_{14}$-$R_{11}$
where $R_{11}$ is as previously defined.

For example, a PGLa like peptide may also have the following structure:

$$\text{-}X_{14}\text{-}Z_{14}\text{-}$$

where $X_{14}$ is as previously defined; and $Z_{14}$ is:
  (i) $R_{11}$; or
  (ii) $R_{11}$-$R_{11}$
where $R_{11}$ is as previously defined.

A PGLa peptide may also have the following structure:

$$(Y_{14})_a\text{-}X_{14}\text{-}(Z_{14})_b$$

where $X_{14}$; $Y_{14}$ and $Z_{14}$ are as previously defined, a is 0 or 1 and b is 0 or 1.

An XPF peptide is either XPF or an analogue or derivative thereof. The XPF peptides preferably include the following basic peptide structure $X_{16}$:

$$\begin{array}{c}-R_{11}-R_{17}-R_{12}-R_{11}-R_{14}-R_{18}-R_{17}-\\R_{11}-R_{14}-R_{12}-R_{11}-R_{11}-R_{12}-\\R_{11}-R_{11}-R_{11}-R_{12}-R_{15}-R_{11}-,\end{array}$$

wherein $R_{11}$, $R_{12}$, $R_{14}$, $R_{15}$ and $R_{17}$ are as previously defined and $R_{18}$ is glutamine or asparagine.

The XPF peptides generally include at least nineteen amino acids and may include up to forty amino acids. Accordingly, the hereinabove described basic peptide structure of XPF may include additional amino acids at the amino end, or at the carboxyl end or at both the amino and carboxyl ends.

Thus, for example, an XPF peptide may include the following structure:

$$\text{-}Y_{16}\text{-}X_{16}\text{-}$$

where $X_{16}$ is as previously defined and $Y_{16}$ is
  (i) $R_{11}$ or
  (ii) $R_{14}$-$R_{11}$
where $R_{11}$ and $R_{14}$ are is as previously defined.

An XPF peptide may include the following structure:

-$X_{16}$-$Z_{16}$- where $X_{16}$ is as previously defined and $Z_{16}$ is
(i) $R_{11}$; or
(ii) $R_{11}$-$R_{18}$; or
(iii) $R_{11}$-$R_{18}$-Proline; or
(iv) $R_{11}$-$R_{18}$-Proline-$R_{12}$ An XPF peptide may also have the following structure:

$$(Y_{16})_a\text{-}X_{16}(Z_{16})_b$$

where $X_{16}$, $Y_{16}$ and $Z_{16}$ are as previously defined: a is 0 or 1 and b is 0 or 1.

Preferred are XPF or PGLa peptides, which are characterized by the following primary amino acid sequence (single letter amino acid code):
PGLa: GMASKAGAIAGKIAKVALKAL (NH₂)
XPF: GWASKIGQTLGKIAKVGLKELIQPK A review of XPF and PGLa can be found in Hoffman et al, *EMBO J.* 2:711–714, 1983; Andreu et al, *J. Biochem.* 149:531–535, 1985; Gibson et al *J. Biol. Chem.* 261:5341–5349, 1986; and Giovannini et al, *Biochem J.* 243:113–120, 1987.

In accordance with yet another embodiment, the peptide employed in conjunction with an antibiotic such as those hereinabove described, or derivatives or analogues thereof may be a CPF peptide or appropriate analogue or derviative thereof.

A basic CPF peptide structure as well as analogues and derivatives thereof are herein sometimes referred to collectively as CPF peptides.

The CPF peptide is preferably one which includes the following peptide structure $X_{30}$:

-$R_{21}$-$R_{21}$-$R_{22}$-$R_{22}$-$R_{21}$-$R_{21}$-$R_{23}$-$R_{21}$-$R_{21}$-$R_{21}$-$R_{23}$-$R_{21}$-$R_{21}$-$R_{24}$-$R_{25}$-$R_{21}$- wherein $R_{21}$ is a hydrophobic amino acid;
$R_{22}$ is a hydrophobic amino acid or a basic hydrophilic amino acid;
$R_{23}$ is a basic hydrophilic amino acid; and
$R_{24}$ is a hydrophobic or neutral hydrophilic amino acid; and
$R_{25}$ is a basic or neutral hydrophilic amino acid.

The hereinabove basic structure is hereinafter symbolically indicated as $X_{30}$.

The hydrophobic amino acids may be Ala, Cys, Phe, Gly, Ile, Leu, Met, Val, Trp, and Tyr.

The neutral hydrophilic amino acids may be Asn, Gln, Ser, and Thr.

The basic hydrophilic amino acids may be Lys, Arg, and His.

The CPF peptide may include only the hereinabove noted amino acids or may include additional amino acids at the amino end or carboxyl end or both the amino and carboxyl end. In general, the peptide does not include more than 40 amino acids.

The CPF peptides including the above basic peptide structure may have from 1 to 4 additional amino acids at the amino end. Accordingly, such preferred peptides may be represented by the structural formula:

$Y_{30}$-$X_{30}$- wherein $X_{30}$ is the hereinabove described basic peptide structure and $Y_{30}$ is (i) $R_{25}$-, or
(ii) $R_{22}$-$R_{25}$; or
(iii) $R_{21}$-$R_{22}$-$R_{25}$; or
(iv) $R_{22}$-$R_{21}$-$R_{22}$-$R_{25}$; preferably Glycine -$R_{21}$-$R_{22}$-$R_{25}$.

wherein $R_{21}$, $R_{22}$, and $R_{25}$ are as previously defined.

The carboxyl end of the basic peptide structure may also have additional amino acids which may range from 1 to 13 additional amino acids.

In a preferred embodiment, the basic structure may have from 1 to 6 additional amino acids at the carboxyl end, which may be represented as follows:

-$X_{30}$-$Z_{30}$ wherein $X_{30}$ is the hereinabove defined basic peptide structure and $Z_{30}$ is
(i) $R_{21}$-,
(ii) $R_{21}$-$R_{21}$-;
(iii) $R_{21}$-$R_{21}$-$R_{24}$;
(iv) $R_{21}$-$R_{21}$-$R_{24}$-$R_{24}$;
(v) $R_{21}$-$R_{21}$-$R_{24}$-$R_{24}$-$R_{26}$;
(vi) $R_{21}$-$R_{21}$-$R_{24}$-$R_{24}$-$R_{26}$-Gln; or
(vii) $R_{21}$-$R_{21}$-$R_{24}$-$R_{24}$-$R_{26}$-Gln-Gln,
wherein $R_{21}$ and $R_{24}$ are as previously defined, and $R_{26}$ is proline or a hydrophobic amino acid.

Preferred peptides may be represented by the following structural formula:

$$(Y_{30})_a\text{-}X_{30}\text{-}(Z_{30})_b$$

wherein $X_{30}$, $Y_{30}$ and $Z_{30}$ are as previously defined and a is 0 or 1 and b is 0 or 1.

Representative examples of CPF peptides which are useful in the present invention have been described in the literature and comprise the following sequences (single letter amino acid code):

(1) GFGSFLGLALKAALKIGANALGGAPQQ
(2) GLASFLGKALKAGLKIGAHLLGGAPQQ
(3) GLASLLGKALKAGLKIGTHFLGGAPQQ
(4) GLASLLGKALKATLKIGTHFLGGAPQQ
(5) GFASFLGKALKAALKIGANMLGGTPQQ
(6) GFGSFLGKALKAALKIGANALGGAPQQ
(7) GFGSFLGKALKAALKIGANALGGSPQQ
(8) GFASFLGKALKAALKIGANLLGGTPQQ

A review of the CPF peptides can be found in Richter, K., Egger, R., and Kreil (1986) J. Biol. Chem. 261, 3676–3680; Wakabayashi, T. Kato, H., and Tachibaba, S. (1985) Nucleic Acids Research 13, 1817–1828; Gibson, B. W., Poulter, L., Williams, D. H., and Maggio, J. E. (1986) J. Biol. Chem. 261, 5341–5349.

CPF peptides which may be employed in the present invention are represented by the following (single letter amino acid code):

G12S3LG4ALKA5LKIG678LGG9(10)QQ

Where:

1 = F, L
2 = G, A
3 = F, L
4 = K, L
5 = A, G, T
6 = A, T
7 = H, N
8 = A, M, F, L
9 = A, S, T

10 = P, L

The numbered amino acids may be employed as described in any combination to provide either a basic CPF peptide structure or an analogue or derivative. The term CPF peptide includes the basic peptide structure as well as analogues or derivatives thereof.

In still another embodiment, the peptide employed in conjunction with an antibiotic such as those hereinabove described, or derivatives or analogues thereof is a cecropin. The cecropins and analogues and derivatives thereof are described in *Ann. Rev. Microbiol* 1987, Vol. 41 pages 103–26, in particular p. 108 and Christensen at al PNAS Vol. 85 p. 5072–76, which are hereby incorporated by reference.

The term cecropin includes the basic structure as well as analogues and derivatives.

In yet another embodiment, the peptide employed in conjunction with an antibiotic such as those hereinabove described, or derivatives or analogues thereof is a sarcotoxin. The sarcotoxins and analogues and derivatives thereof are described in *Molecular Entomology*, pages 369–78, in particular p. 375 Alan R. Liss Inc. (1987), which is hereby incorporated by reference.

The term sarcotoxin includes the basic materials as well as analogues and derivatives.

The bacitracins which may be employed in accordance with the present invention tend to be hydrophilic and water-soluble. The preferred bacitracin is bacitracin A, which is of the following structure:

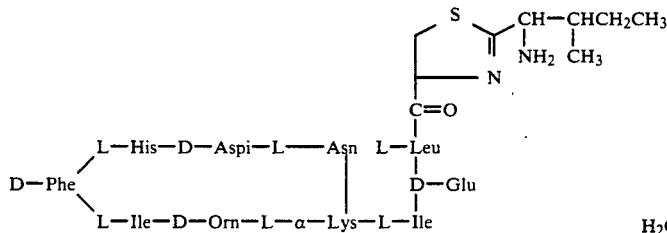

Preferred aminoglycoside antibiotics which may be employed are tobramycin and the gentamicins. Tobramycin is of the following structure:

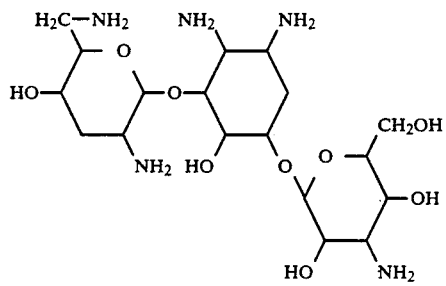

The gentamicins (Gentamicin $C_1$, Gentamicin $C_2$, and Gentamicin $C_{1a}$), as well as netilmicin, have the following basic structure:

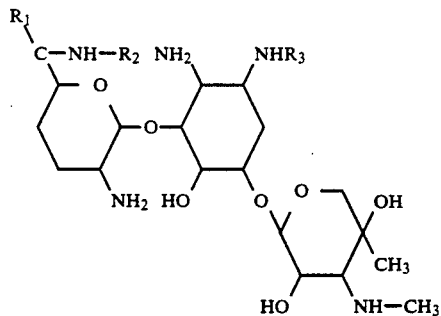

For Gentamicin $C_1$, $R_1$ and $R_2$ each are $CH_3$, the $C_4$–$C_5$ bond is a single bond, and $R_3$ is H. For Gentamicin $C_2$, $R_1$ is $CH_3$, $R_2$ and $R_3$ each are H, and the $C_4$–$C_5$ bond is a single bond. For Gentamicin $C_{1a}$, $R_1$, $R_2$ and $R_3$ each are H, and the $C_4$–$C_5$ bond is a single bond. For netilmicin, $R_1$ and $R_2$ each are H, $R_3$ is $C_2H_5$, and the $C_4$–$C_5$ bond is a double bond.

Other aminoglycosides which may also be employed within the scope of the present invention include, but are not limited to, kanamycin and amikacin, as well as netilmicin, gramacidin, polymyxin, vancomycin, and teichoplanin. Kanamycin and amikacin are both of the following basic structure:

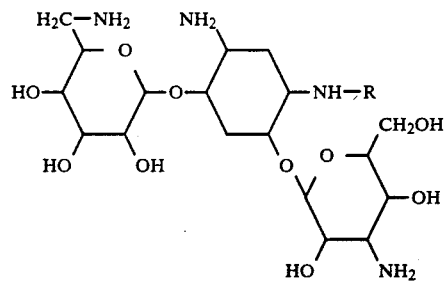

For kanamycin, R is H, and for amikacin, R is:

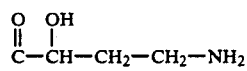

Erythromycin, which is isolated from *Streptomyces erythreus*, is a member of a group of compounds known as macrolides. The basic structure is a large lactone ring to which unusual sugars are attached. The term "macrolide" refers to a large ring formed from a chain of 14 to 20 carbon atoms by lactone condensation of a carboxyl and hydroxyl group. Other macrolides include oleandomycin, spiramycin, kitasamycin, and carbonmycin. Erythromycin is of the following structure:

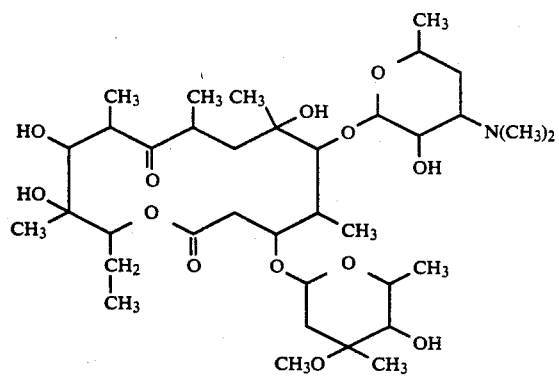

It is also to be understood that other macrolide antibiotics, such as roxythromycin, clarithromycin, and others hereinabove described, may be employed as well.

For purposes of illustration of examples of other macrolide structures, the following examples, in addition to the above structure of erythromycin, are given below.

Rokitamycin is of the following structure:

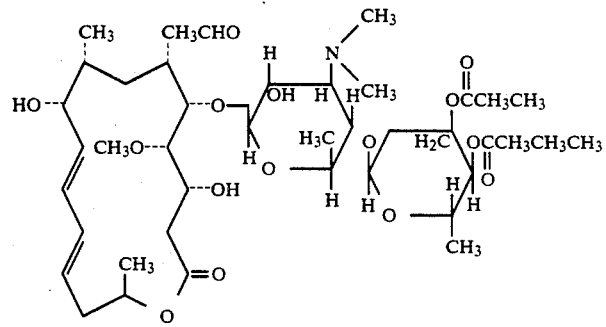

CGP-7040, a benzapiperazinyl rifamycin, has the following structure:

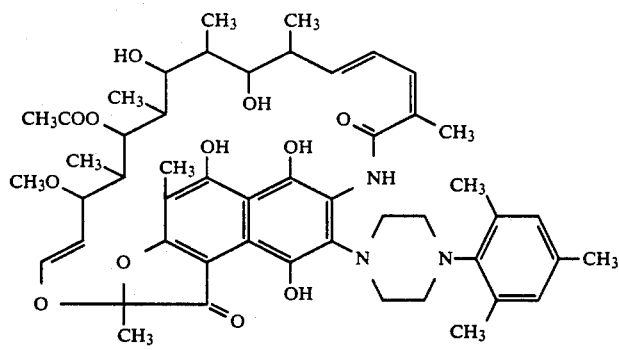

It is to be understood, however, that the scope of the present invention is not to be limited to the specific macrolides or macrolide structures hereinabove described.

Preferred penicillins which may be employed in accordance with the present invention are benzyl penicillin (penicillin G) and ampicillin (alpha-amino-benzyl penicillin). Benzyl penicillin is of the following structure:

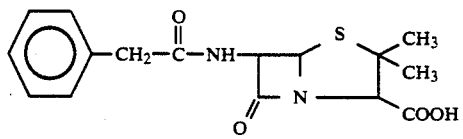

Ampicillin is of the following structure:

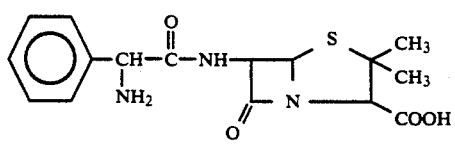

A preferred monobactam which may be employed in accordance with the present invention is aztreonam, which is of the following structure:

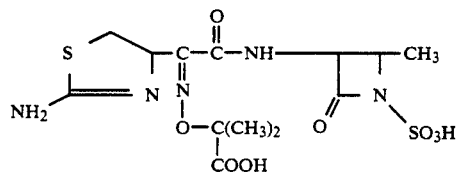

It is to be understood, however, that the scope of the invention is not to be limited to the specific antibiotics and antibiotic structures hereinabove described.

The present invention will be further described with respect to the following examples, however, the scope of the invention is not to be limited thereby.

EXAMPLE 1

S. aureus organisms are grown to mid log phase, and then diluted to $10^3$ organisms/ml in ½ strength trypticase soy broth. After the incubation of the organisms, the minimal inhibitory concentration in ug/ml for Z-52 MG-2(amide-terminated), PGLa, CPF Z-50, A-97, Magainin II, and Z-74 peptides, against S. aureus was measured when each peptide was added alone to the organisms. "MG-2 (amide)" is amide-terminated Magainin II, and "Magainin II" is carboxy-terminated Magainin II. A-97 peptide is of the following structure:

GIGKFLHSAGKFGKAFVKIMKS-amide

Z-74 peptide is of the following structure:

B-Ala-GIGKFLHAAKKFAKAFVAEIMNS-amide

The PGLa peptide is of the following structure:

GMASKAGAIAGKIAKVALKAL-amide.

The minimal inhibitory concentration (MIC) for each peptide was then measured when 20% of the minimal inhibitory concentration of bacitracin, tobramycin or gentamicin, respecitvely, is added to the organisms along with the peptide. The gentamicin employed is a mixture of Gentamicin $C_1$, Gentamicin $C_{1a}$, and Gentamicin $C_2$. For Examples 1–3, the MIC values for bacitracin are 2 μg/ml against S. aureus, 64 μg/ml against E. coli, and >256 μg/ml against Pseudomanas aeruginosa. The MIC values for gentamicin are 256 μg/ml against S. aureus, 2 μg/ml against E. coli, and >256 μg/ml against P. aeruginosa. The MIC values for tobramycin are >256 μg/ml against S. aureus, 2 μg/ml against E. coli, and 128 μg/ml against P. aeruginosa. CPF Z-50 peptide has structure number (8) of the CPF peptides hereinabove described. Z-52 peptide is of the structure $(ALSK)_6NH_2$. The minimal inhibitory concentrations are given below in Table I.

TABLE I

| Peptide | MIC Peptide Alone | Bacitracin | With Added Antibiotic Gentamicin | Tobramycin |
|---|---|---|---|---|
| Z-52 | 32 | 8 | 16 | 16 |
| MG-2 amide | 256 | 32 | 4 | 32 |
| PGLa | 32 | 16 | 2 | 32 |
| A-97 | 32 | 16 | 4 | 32 |
| Magainin 2 | 256 | 128 | 4 | 32 |
| Z-50 | 16 | 16 | 2 | 8 |
| Z-74 | 16 | 16 | 4 | 8 |

EXAMPLE 2

E. coli organisms were incubated according to the procedure described in Example 1. After the incubation, the minimal inhibitory concentrations against E. coli of each of the peptides described in Example 1 alone, as well as of each peptide when employed in combination with 20% of the MIC for bactracin, were then measured. The results are given in Table 2 below.

TABLE 2

| Peptide | MIC Peptide Alone | Peptide with Bacitracin |
|---|---|---|
| Z-52 | 8 | 8 |
| MG-2 amide | 16 | 4 |
| PGLa | 16 | 8 |
| Z-50 | 16 | 16 |
| A-97 | 8 | 4 |
| Magainin II amide) | 32 | 8 |
| Z-74 | 16 | 8 |

EXAMPLE 3

In this example, P. aeruginosa organisms were incubated according to the procedure described in Example 1. After the incubation, the minimal inhibitory concentrations of the peptides hereinabove described alone, as well as the peptides in combination with 20% of the MIC of bacitracin, were then measured. The results are given below in Table 3.

TABLE 3

| Peptide | MIC Peptide Alone | Peptide with Bacitracin |
|---|---|---|
| Z-52 | 16 | 2 |
| MG-2 amide | 128 | 8 |
| PGLa | 64 | 8 |
| Z-50 | 32 | 4 |
| A-97 | 32 | 4 |
| Magainin II | 256 | 16 |
| Z-74 | 16 | 16 |

EXAMPLE 4

In this example, E. coli or P. aeruginosa organisms were incubated according to the procedure described in Example 1. After, the incubation, the minimal inhibitory concentrations of the peptides hereinabove described alone, as well as the peptides in combination with 20% of the minimal inhibitory concentrations (MIC) of benzyl penicillin or ampicillin, were then measured. The MIC of benzyl penicillin against E. coli is 64 μg/ml, and of ampicillin against E. coli is 4 μg/ml. The results are given below in Table 4.

TABLE 4

| Peptide | MIC Peptide alone | Peptide and Benzyl penicillin | Peptide and Ampicillin |
|---|---|---|---|
| E. coli- | | | |
| Z-52 | 16 | | 16 |
| Mg 2-amide | 64 | 32 | 8 |
| PGLa | 32 | | 16 |
| Magainin II | 64 | 32 | 16 |
| Z-50 | 32 | | 8 |
| A-97 | 32 | 16 | 16 |
| Z-74 | 4 | | 8 |
| P. aeruginosa- | | | |
| PGLa | 128 | 32 | 32 |
| Mg-2 amide | 256 | 128 | 128 |

EXAMPLE 5

E. coli and P. aeruoginosa organisms were incubated according to the procedure described in Example 1. After the incubation, the minimal inhibitory concentrations of the peptides hereinabove described alone, as well as the peptides in combination with 20% of the MIC of the monobactam antibiotic aztreonam, were then measured. The MIC of aztreonam against *E. coli* is a 2 μg/ml, and against *P. aeruginosa* is 8 μg/ml. The results are given below in Table 5.

TABLE 5

| Peptide | MIC | |
|---|---|---|
| | Peptide alone | Peptide with Aztreonam |
| *E. coli*- | | |
| Z-52 | 16 | 2 |
| Mg 2-amide | 64 | 32 |
| PGLa | 32 | 4 |
| Z-50 | 32 | 8 |
| A-97 | 32 | 8 |
| Magainin II | 64 | 16 |
| Z-74 | 4 | 8 |
| *P. aeruginosa*- | | |
| Z-52 | 32 | 32 |
| Mg-2 amide | 128 | 64 |
| PGLa | 128 | 64 |
| Z-50 | 64 | 32 |
| A-97 | 32 | 32 |
| Magainin II | 256 | 128 |
| Z-74 | 32 | 8 |

The above results indicate that when one of the biologically active ion-channel forming peptides hereinabove described is added in combination with bacitracin, tobramycin, gentamicin, benzyl penicillin, ampicillin, or aztreonam, in an amount of 20% of the MIC of these antibiotics, against *S. aureus, E. coli*, or *P. aeruginosa*, there is, in most cases, a resulting synergy between the peptide and the antibiotic. In most cases, less peptide and less antibiotic may be used against these organisms when peptide and antibiotic are employed in combination, than if peptide or antibiotic alone were employed.

EXAMPLE 6

In this example, the effect of a combination of erythromycin and biologically active amphiphilic ion channel-forming peptide will be measured against *K. pneumoniae, P. aeruginosa, E. coli*, and *S. aureus*.

For each of the organisms listed in Table 6 below, $10^5$ organisms were mid-log inoculated into 200 ml of one-half strength trypticase soy broth. The organisms were incubated for 15 hrs. at 37° C. After the incubation of the organisms, the minimal inhibitory concentration in μg/ml for Magainin II (amide-terminated), shown as MGN2, CPF Z-50 (amide-terminated) peptide , Z-52 (amide-terminated) peptide, against each species of organism was measured wherein 10 μg/ml of erythromycin was added and wherein no erythromycin was added. The minimal inhibitory concentration of erythromycin alone against each species of organism was also measured. The minimal inhibitory concentrations in μg/ml are given below in Table 6. For purposes of explanation, the "+" and "−" signs below the "Erythromycin (10 μg/ml)" column indicate the presence or absence, respectively, of erythromycin administered in combination with one of the biologically active peptides. *K. pneumoniae, P. aeruginosa*, and *E. coli* are Gram-negative bacteria.

TABLE 6

| Organism | Erthromycin (10 μg/ml) | Minimal Inhibitory Concentration (μg/ml) | | | |
|---|---|---|---|---|---|
| | | MGN2 amide | CPF Z-50 amide | Z-52 amide | Erythromycin |
| *K. Pneumoniae* | − | 5 | <0.5 | 1.5 | >100 |
| | + | <0.5 | <0.5 | <0.5 | |
| *P. aeruguinosa* | − | 50–100 | <5.0 | 5–15 | >100 |

TABLE 6-continued

| Organism | Erthromycin (10 μg/ml) | Minimal Inhibitory Concentration (μg/ml) | | | |
|---|---|---|---|---|---|
| | | MGN2 amide | CPF Z-50 amide | Z-52 amide | Erythromycin |
| *E. coli* | + | <5.0 | <0.5 | <1.5 | |
| | − | 5 | <5.0 | 1.5 | >100 |
| | + | 0.5 | <0.5 | <0.5 | |

The above results show that when one of the biologically active ion channel-forming peptides shown in Table 6 is added to 10 μg/ml of erythromycin, such as a combination of peptide and erythromycin is effective against the Gram-negative organisms shown, whereas greater than 100 μg/ml of erythromycin alone is required for effective biological activity against these Gram-negative organisms. The addition of erythromycin to the biologically active peptides also enables one to use less of the biologically active peptide against Gram-negative organisms. Thus, there is provided a synergistic effect against Gram-negative organisms when erythromycin and a biologically active amphiphilic ion channel-forming peptide are administered to inhibit growth of Gram-negative organisms.

It was also found that a concentration from about 0.6 μg/ml to about 1.25 μg/ml of erythromycin alone was required for effective biological activity against *S. aureus*, a Gram-positive organism, and that greater than 250 μg/ml of amide-terminated Magainin II alone was required for effective biological activity against *S. aureus*. A combination of 10 μg/ml of amide-terminated Magainin II and 0.03 μg/ml of erythromycin, however, also showed effective biological activity against *S. aureus*. Thus, it has also been shown that a synergistic effect against Gram-positive organisms is also obtained when erythromycin and a biologically active amphiphilic ion channel forming peptide are administered to inhibit growth of Gram-positive organisms. The addition of erythromycin to the biologically active peptide enables one use less of the biologically active peptide against a Gram-positive organism.

The peptide and antibiotic such as those hereinabove described, may be employed for treating a wide variety of hosts. In accordance with a preferred embodiment, a host is an animal, and such animal may be a human or non-human animal. It is also possible to administer the peptide and antibiotic in separate forms. For example, the antibiotic may be administered systemically and the peptide may be administered topically.

The peptide and/or antibiotic such as those hereinabove described, may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide and/or antibiotic such as those hereinabove described may also be used in combination with adjuvants, protease inhibitors, or compatible drugs where such a combination is seen to be desirable or advantageous in controlling infection caused by harmful microorganisms.

When the peptide is administered topically, it is administered in combination with a water-soluble vehicle, said water-soluble vehicle being in the form of an ointment, cream, lotion, paste, or the like. Examples of water-soluble vehicles which may be employed include, but are not limited to, glycols, such as polyethylene glycol, hydroxycellulose, and KY Jelly. The water-soluble vehicle is preferably free of an oily substance.

The combination of peptide and antibiotic of the present invention may be administered to a host; in particular an animal, in an effective antibiotic amount. When used to inhibit growth of bacterial cells, the combination, whether administered as a mixture or separately, is employed in an effective antibacterial amount. When used to inhibit growth of fungi, such components are administered in an effective antifungal amount.

As representative examples of administering the peptide and antibiotic for topical or local administration, the peptide could be administered in an amount of from about 0.1% to about 10% weight to weight; and the antibiotic is delivered in an amount of from about 0.1% to about 10% weight to weight.

Numerous modifications and variations of the present invention are possible in light of the above teachings and, therefore, within the scope of the appended claims, the invention may be practiced otherwise than as particularly described.

What is claimed is:

1. A process of inhibiting growth of a target cell in a host, comprising:
   administering to a host at least one biologically active amphiphilic peptide, said peptide being an ion channel-forming peptide; and
   an antibiotic selected from the class consisting of a bacitracin, an aminoglycoside antibiotic, a penicillin, a monobactam, a hydrophobic, antibiotic, a 50-S ribosome inhibitor, and an, antibiotic having a large lipid-like lactone ring, said biologically active amphiphilic peptide and said antibiotic being administered in a combined amount effective to inhibit growth of a target cell in a host.

2. The process of claim 1 wherein the peptide is a basic polypeptide having at least sixteen amino acids, wherein said basic polypeptide includes at least eight hydrophobic amino acids and at least eight hydrophilic amino acids.

3. The process of claim 2 wherein said polypeptide comprises a chain of at least four groups of amino acids, each of said at least four groups consisting of four amino acids, wherein two of the four amino acids in each group are hydrophobic amino acids, and two of the four amino acids in each group are hydrophilic amino acids, with at least one of the hydrophilic amino acids in each group being a basic hydrophilic amino acid and the other hydrophilic amino acid being a basic or neutral hydrophilic amino acid.

4. The process of claim 3 wherein each of said groups of four amino acids is of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid any may be the same or different.

5. The process of claim 1 wherein the peptide is a magainin peptide.

6. The process of claim 5 wherein said magainin peptide includes the following basic peptide structure:

$$-R_{11}-R_{11}-R_{12}-R_{13}-R_{14}-R_{12}-R_{11}-R_{14}-R_{11}-R_{12}-R_{11}-R_{11}-R_{11}-R_{14a}-(R_{15})n-R_{14a}-R_{14}-$$

wherein $R_{11}$ is a hydrophobic amino acid, $R_{12}$ is a basic hydrophilic amine acid, $R_{13}$ is a hydrophobic, neutral hydrophilic, or basic hydrophilic amino acid, $R_{14}$ and $R_{14}$ are hydrophobic or basic hydrophilic amino acids, $R_{15}$ is glutamic acid or aspartic acid, a hydrophobic amino acid, or a basic hydrophilic amino acid, and n is 0 or 1.

7. The process of claim 6 wherein $R_{13}$ is a hydrophobic or neutral hydrophilic amino acid.

8. The process of claim 6 wherein $R_{14a}$ is a hydrophobic amino acid.

9. The process of claim 6 wherein $R_{15}$ is glutamic acid or aspartic acid.

10. The process of claim 5 wherein said magainin peptide is of the following basic peptide structure:

$$-R_{14}-R_{11}-R_{14a}-R_{12}-R_{11}-R_{11}-R_{12}-R_{13}-R_{11}-R_{14}-R_{12}-R_{11}-R_{11}-R_{12}-,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, and $R_{14}$ and $R_{14a}$ are hydrophobic or basic hydrophilic amino acids.

11. The process of claim 10 wherein $R_{13}$ is a hydrophobic or neutral hydrophilic amino acid.

12. The process of claim 10 wherein $R_{14a}$ is a hydrophobic amino acid.

13. The process of claim 1 wherein the peptide is a cecropin.

14. The process of claim 1 wherein the peptide is a sarcotoxin.

15. The process of claim 1 wherein the peptide is a XPF peptide.

16. The process of claim 1 wherein the peptide is a PGLa peptide.

17. The process of claim 1 wherein the peptide is a CPF peptide.

18. The process of claim 1 wherein said antibiotic is a bacitrasin or an analogue or derviative thereof.

19. The process of claim 1 wherein said antibiotics is an aminoglycoside antibiotic.

20. The process of claim 19 wherein said amino glycoside antibiotic is tobramycin or a derivative or analogue thereof.

21. The process of claim 19 wherein said aminoglycoside antibiotic is a gentamicin or a derivative or analogue thereof.

22. The process of claim 1 wherein said antibiotic is a penicillin or derivative or analogue thereof.

23. The process of claim 1 wherein said antibiotic is a monobactam or derivative or analogue thereof.

24. The process of claim 1 wherein said antibiotic is a hydrophobic antibiotic.

25. The process of claim 24 wherein said hydrophobic antibiotic is a macrolide antibiotic.

26. The process of claim 25 wherein said macrolide antibiotic is erythromycin or a derivative or analogue thereof.

27. The process of claim 1 wherein said antibiotic is a 50-S ribosome inhibitor.

28. The process of claim 1 wherein said antibiotic has a large lipid-like lactone ring.

29. A composition comprising:
   (a) at least one biologically active peptide, said peptide being an ion channel-forming peptide; and (b) an antibiotic selected from the class consisting of a bacitracin, an aminoglycoside antibiotic, a penicillin, a monobactam, a hydrophobic antibiotic, a 50-S ribosome inhibitor, an antibiotic having a large lipid-like lactone ring, and derivatives and analogues thereof, and (c) an acceptable pharmaceutical carrier, wherein said components (a) and (b) are present in a combined amount effective to inhibit growth of a target cell in a host.

30. The composition of claim 29 wherein the peptide is a basic polypeptide having at least sixteen amino acids, wherein said basic polypeptide includes at least eight hydrophobic amino acids and at least eight hydrophilic amino acids.

31. The composition of claim 30 wherein said polypeptide comprises a chain of at least four groups of amino acids, each of said at least four groups consisting of four amino acids, wherein two of the four amino acids in each group are hydrophobic amino acids, and two of the four amino acids in each group are hydrophilic amino acids, with at least one of the hydrophilic amino acids in each group being a basic hydrophilic amino acid and the other hydrophilic amino acid being a basic or neutral hydrophilic amino acid.

32. The composition of claim 31 wherein each of said groups of four amino acids is of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different.

33. The composition of claim 29 wherein the peptide is a magainin peptide.

34. The composition of claim 33 wherein said magainin peptide includes the following basic peptide structure:

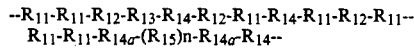

wherein $R_{11}$ is a hydrophobic amino acid, $R_{12}$ is a basic hydrophilic amino acid, $R_{13}$ is a hydrophobic, neutral hydrophilic, or a basic hydrophilic amino acid, $R_{14}$ and $R_{14a}$ are hydrophobic or basic hydrophilic amino acids, $R_{15}$ is glutamic acid or aspartic acid, a hydrophobic amino acid, or a basic hydrophilic amino acid, and n is 0 or 1.

35. The composition of claim 34 wherein $R_{13}$ is a hydrophobic or basic hydrophilic amino acid.

36. The composition of claim 34 wherein $R_{14a}$ is a hydrophobic amino acid.

37. The composition of claim 34 wherein $R_{15}$ is glutamic acid or aspartic acid.

38. The composition of claim 33 wherein said magainin peptide is of the following basic peptide structure:

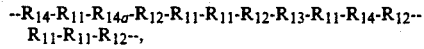

wherein $R_{11}$ is a hydrophobic amino acid, $R_{12}$ is a basic hydrophilic amino acid, $R_{13}$ is a hydrophobic, neutral hydrophilic, or basic hydrophilic amino acid, and $R_{14}$ and $R_{14a}$ are hydrophobic or basic hydrophilic amino acids.

39. The composition of claim 38 wherein $R_{13}$ is a hydrophobic or basic hydropholic amino acid.

40. The composition of claim 38 wherein $R_{14a}$ is a hydrophobic amino acid.

41. The composition of claim 29 wherein the peptide is a cecropin.

42. The composition of claim 29 wherein the peptide is a sarcotoxin.

43. The composition of claim 29 wherein the peptide is a XPF peptide.

44. The composition of claim 29 wherein the peptide is a PGLa peptide.

45. The composition of claim 29 wherein the peptide is a CPF peptide.

46. The composition of claim 29 wherein said antibiotic is a bacitracin or a derivative or analogue thereof.

47. The composition of claim 29 wherein said antibiotic is an aminoglycoside antibiotic.

48. The composition of claim 47 wherein said aminoglycoside antibiotic is tobramycin or a derivative or analogue thereof.

49. The composition of claim 47 wherein said aminoglycoside antibiotic is a gentamicin or a derivative or analogue thereof.

50. The composition of claim 29 wherein said antibiotic is a penicillin or derivative or analogue thereof.

51. The composition of claim 29 wherein said antibiotic is a monobactam or derivative or analogue thereof.

52. The composition of claim 29 wherein said antibiotic a hydrophobic antibiotic.

53. The composition of claim 52 wherein said hydrophobic antibiotic is a macrolide antibiotic.

54. The composition of claim 53 wherein said macrolide antibiotic is erythromycin or a derivative or analogue thereof.

55. The composition of claim 29 wherein said antibiotic is a 50-S ribosome inhibitor.

56. The composition of claim 29 wherein said antibiotic has a large lipid-like lactone ring.

57. The process of claim 1 wherein each of said peptide and said antibiotic is administered in an amount ineffective in inhibiting growth of a target cell in a host if administered alone to a host.

58. The composition of claim 29 wherein each of said components (a) and (b) are present in an amount ineffective to inhibit growth of a target cell if administered alone to a host.

59. The process of claim 22 wherein said penicillin is benzyl penicillin.

60. The process of claim 22 wherein said penicillin is ampicillin.

61. The process of claim 23 wherein said monobactam is aztreonam.

62. A process of inhibiting growth of a target cell in a host, comprising:
administering to a host at least one biologically active amphiphilic peptide selected from the group consisting of:
(a) a magainin peptide;
(b) a PGLa peptide;
(c) an XPF peptide;
(d) a CPF peptide;
(e) a cecropin;
(f) a sarcotoxin; and
(g) a basic polypeptide having at least sixteen amino acids, wherein said basic polypeptide includes at least eight hydrophobic amino acids and at least eight hydrophilic amino acids; and an antibiotic selected from the class consisting of a bacitracin, an aminoglycoside antibiotic, a penicillin, a monobactam, a hydrophobic antibiotic, a 50-S ribosome inhibitor, and an antibiotic having a large lipid-like lactone ring, said biologically active amphiphilic peptide and said antibiotic being administered in a combined amount effective to inhibit growth of a target cell in a host.

63. The process of claim 62 wherein the peptide is a magainin peptide.

64. The process of claim 63 wherein said magainin peptide includes the following basic peptide structure:

$$-R_{11}-R_{11}-R_{12}-R_{13}-R_{11}-R_{14}-R_{12}-R_{11}-R_{14}-R_{11}-R_{12}-$$
$$R_{11}-R_{11}-R_{11}-R_{14a}-(R_{15})_n-R_{14a}-R_{14}-,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ $R_{14a}$ are hyrophobic or basdic hydrophilic amino acids, $R_{15}$ is glutamic acid or aspartic acid, a hydrophobic amino acid, or a basic hydrophilic amino acid, and n is 0 or 1.

65. The process of claim 63 wherein said magainin peptide includes the following basic peptide structure:

$$-R_{14}-R_{11}-R_{14a}-R_{12}-R_{11}-R_{11}-R_{12}-R_{13}-R_{11}-R_{14}-R_{12}-$$
$$R_{11}-R_{11}-R_{12}-$$

wherein $R_{11}$ is hydrophobic amino acid, $R_{12}$ is a basic hydrophilic amino acid, $R_{13}$ is hydrophobic, neutral hydrophilic, or basic hydrophilic amino acid, and $R_{14}$ and $R_{14a}$ are hydrophobic or basic hydriophilic amino acids.

66. A composition comprising:
(a) at least one biologically active amphiphilic peptide selected form the group consisting of:
(i) a magainin peptide;
(ii) a PGLa peptide;
(iii) an XPF peptide;
(iv) a CPF peptide;
(v) a cecropin;
(vi) a sacrotoxin; and
(vii) a basic polypeptide having at least sixteen amino acids, wherein said basic polypeptide includes at least eight hydrophobic amino acids and at least eight hydrophilic amino acids; and
(b) an antibiotic selected from the class consisting of a bacitracin, an aminoglycoside antibiotic, a penicillin, a monobactam, a hydrophobic antibiotic, a 50-S ribosome inhibitor, and an antibiotic having a large lipid-like lactone ring, and
(c) an acceptable pharmaceutical carrier, wherein said components (a) and (b) are present in a combined amount effective to inhibit growth of a target cell in a host.

67. The composition of claim 66 wherein the peptide is a magainin peptide.

68. The composition of claim 67 wherein said magainin peptide includes the following basic peptide structure:

$$-R_{11}-R_{11}-R_{12}-R_{13}-R_{11}-R_{14}-R_{12}-R_{11}-R_{14}-R_{11}-R_{12}-$$
$$R_{11}-R_{11}-R_{11}-R_{14a}(R_{15})_n-R_{14a}-R_{14}-,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ and $R_{14a}$ are hydrophobic or basic hydrophilic amino acids, $R_{15}$ is glutamic acid or aspartic acid, a hydrophobic amino acid, or a basic hydrophilic amino acid, and n is 0 or 1.

69. The composition of claim 67 wherein said magainin peptide includes the following basic peptide structure:

$$-R_{14}-R_{11}-R_{14a}-R_{12}-R_{11}-R_{11}-R_{12}-R_{13}-R_{11}-R_{14}-R_{12}-$$
$$R_{11}-R_{11}-R_{12}-,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, and $R_{14}$ and $R_{14a}$ are hydrophobic or basic hydrophilic amino acids.

70. The process of claim 1 wherein the target cell is a Gram-negative bacterium.

71. The process of claim 1 wherein the target cell is a Gram-positive bacterium.

72. The composition of claim 29 wherein the target cell is a Gram-negative bacterium.

73. The composition of claim 29 wherein the target cell is a Gram-positive bacterium.

74. The process of claim 62 wherein the target cell is a Gram-negative bacterium.

75. The process of claim 62 wherein the target cell is a Gram-positive bacterium.

76. The composition of claim 66 wherein the target cell is a Gram-negative bacterium.

77. The composition of claim 66 wherein the target cell is a Gram-positive bacterium.

* * * * *